United States Patent [19]

Binard

[11] Patent Number: 4,552,134

[45] Date of Patent: Nov. 12, 1985

[54] EQUIPMENT FOR DETERMINING THE POSITION OF A METAL BODY IN A MEDIUM WITH LOW ELECTRIC CONDUCTIVITY

[75] Inventor: Luc André M. G. Binard, Woluwe Saint Pierre, Belgium

[73] Assignee: Studiecentrum voor Kernenergie, S.C.K., Brussels, Belgium

[21] Appl. No.: 502,936

[22] Filed: Jun. 10, 1983

[30] Foreign Application Priority Data

Jun. 17, 1982 [LU] Luxembourg ............................ 84209

[51] Int. Cl.[4] ............................................... A61B 5/04
[52] U.S. Cl. .................................. 128/1.5; 128/92 A; 128/774; 324/233; 324/243
[58] Field of Search ..................... 128/1.3–1.5, 128/653, 721, 774, 775, 777, 779–782, 92 A, 92 G, 92 ED; 324/207–208, 228, 233, 243, 248; 340/551

[56] References Cited

U.S. PATENT DOCUMENTS

| 3,305,711 | 2/1967 | Quittner | 324/208 X |
| 3,371,272 | 2/1968 | Stanton | 128/1.5 |
| 3,827,291 | 8/1974 | McCalvey | 324/208 X |
| 4,088,952 | 5/1978 | Sikora | 324/207 |
| 4,270,545 | 6/1981 | Rodler | 128/653 |
| 4,303,883 | 12/1981 | Mori et al. | 324/208 |
| 4,371,836 | 2/1983 | Nickel et al. | 128/777 X |
| 4,445,501 | 5/1984 | Bresler | 324/233 X |

FOREIGN PATENT DOCUMENTS

| 2330368 | 6/1977 | France | 128/774 |
| 235912 | 1/1969 | U.S.S.R. | 128/774 |

Primary Examiner—Kyle L. Howell
Assistant Examiner—Francis J. Jaworski
Attorney, Agent, or Firm—Stevens, Davis, Miller & Mosher

[57] ABSTRACT

The equipment for determining the position of a metal pin in a bone comprises a support, a radiating self-induction coil mounted on the support and two receiving self-induction coils mounted on the support. A receiving coil is arranged on either side of the radiating coil but the space between the receiving coils facing the radiating coil remains free. The radiating coil is supplied by an oscillator with a frequency of about 30 kHz. The receiving coils control signaling members according to the phase-shift of signals generated by the receiving coils.

14 Claims, 8 Drawing Figures

EQUIPMENT FOR DETERMINING THE POSITION OF A METAL BODY IN A MEDIUM WITH LOW ELECTRIC CONDUCTIVITY

BACKGROUND OF THE INVENTION

This invention relates to an equipment for determining the position of a metal body in a medium with low electric conductivity, which comprises:
a support,
a radiating self-induction coil mounted on the support,
two receiving self-induction coils mounted on the support, said coils having parallel axes, the receiving coils being arranged symmetrically relative to the radiating coil, and the symmetry planes of the receiving coils at right angle to the axes thereof coinciding with one another and differing from the symmetry plane of the radiating coil at right angle to the axis thereof,
a connection to a current source for said radiating coil, signaling members, and
a connection between the receiving coils and said signaling members.

An equipment of this kind is known from U.S. Pat. No. 2,228,293. In the embodiment according to FIG. 3 in this patent, the equipment comprises three radiating coils lying respectively on the three legs of an E-shaped core. Said coils are fed with D.C. and are series connected in such a way that the magnetic flux generated in the center coil has the opposite polarity relative to that magnetic flux generated in the other coils. Two receiving or sensing coils, series-connected, are mounted on the outer core arms in the extension of the radiating coils mounted thereon. The equipment comprises means sensing the changes in the voltage being induced in the receiving coils due to changes in the reluctance of the magnetic field being generated by the movement of a metal body inside said field.

Said equipment which is designed to sense a metal object inside a moving mass, does not allow localizing a metal body inside a material with a low electric conductivity with a high accuracy as required when performing operations on human bodies, which lies for example in the range of a fraction of millimeter. Moreover, the relative arrangement of the coils in this known equipment is such as to prevent arranging the support with the coils thereof in a suitable position for the strength of the signal controlling the signaling members to increase together with the lack of symmetry of the metal object relative to the coils.

The invention has for an object to provide an equipment which allows due to the mechanical and electric design thereof, an optimum localizing of a metal object.

THE INVENTION

For this purpose the current source is an A.C. source, the space between the receiving coils facing the radiating coil remains free, and the connection between the receiving coils and the signaling members controls said members according to the phase-shift of those signals being generated by the receiving coils.

The A.C. source comprises preferably an oscillator e.g. with a frequency in the range of 30 kHz.

It is to be noted that the equipment according to the invention allows more particularly to localize very accurately a metal pin which is entered into the medullary channel of a broken bone.

U.S. Pat. No. 4,281,649 included herein by way of reference describes the fitting of a pin into the medullary channel of a broken bone, and the arrangement of two cross-pins at both ends of the pin through the bone and the holes provided therefor in the pin.

According to this patent, piercing the bone to fit the cross-pins and fitting said pins are performed by using a template fast to the pin.

Experience has shown that piercing the bone for fitting the near cross-pin and said fitting may be performed by using this template fast to the pin, but said template cannot be used when piercing the bone to fit the distal cross-pin and during said fitting unless the medullary channel of the broken bone is accurately straight, which is but seldom the case.

Drilling the bone for fitting the distal cross-pin and fitting said cross-pin consequently require another means to locate very accurately the pin under every circumstance.

The equipment according to the invention as defined above comprises such means.

In an advantageous embodiment of the invention, the spacing between the symmetry plane of the receiving coils and the symmetry plane of the radiating coil lies in the range from 1 to 10 cm, preferably in the range from 6 to 7 cm, the radiating coil height is about 1 cm, the receiving coil height is about 2 to 3 cm, and the free spacing between the receiving coils is in the range from 9 to 13 cm.

In a preferred embodiment of the invention, the support comprises an arm a symmetry plane of which encloses the radiating coil axis and lies at right angle to that plane defined by the receiving coil axes, the radiating coil and the arm are provided with a channel coaxial with the radiating coil, the arm is moreover provided with a series of holes which lie in parallel relationship with the axes and the axis of which lies in said symmetry plane, and the A.C. source and the signaling members are part of an electronic device the coils are connected to by cables.

Other details and features of the invention will stand out from the description of an equipment for determining the position of a metal body in a medium with low electric conductivity according to the invention, given hereafter by way of non limitative example and with reference to the accompanying drawings.

DRAWINGS

In the various figures, the same reference numerals pertain to the same elements.

DESCRIPTION OF A PREFERRED EMBODIMENT

Figure 1:
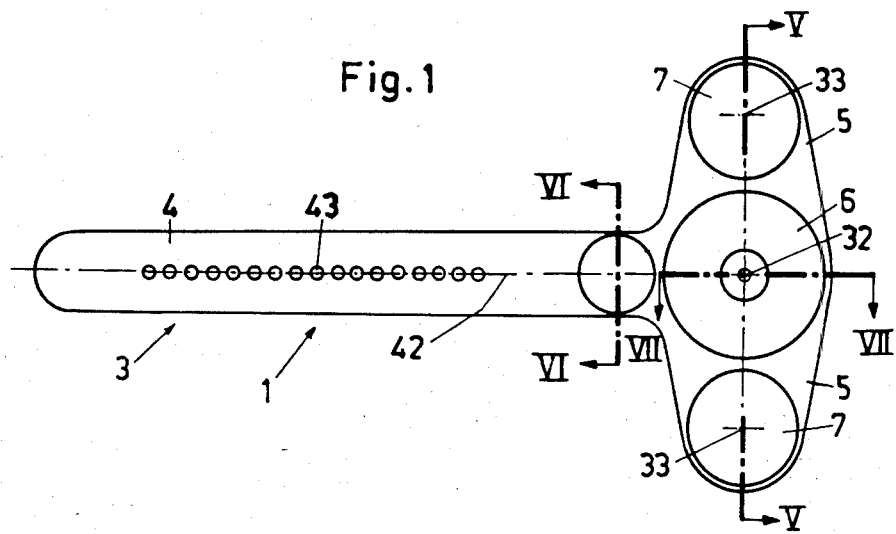
FIG. 1 is a plan view of part of an equipment to determine the position of a metal body inside a medium with low electric conductivity according to the invention.
Figure 2:
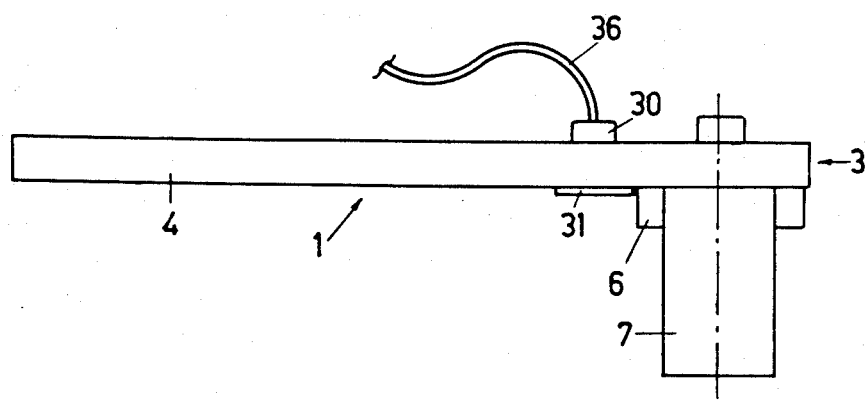
FIG. 2 is an elevation view of the equipment part as shown in FIG. 1.
Figure 3:
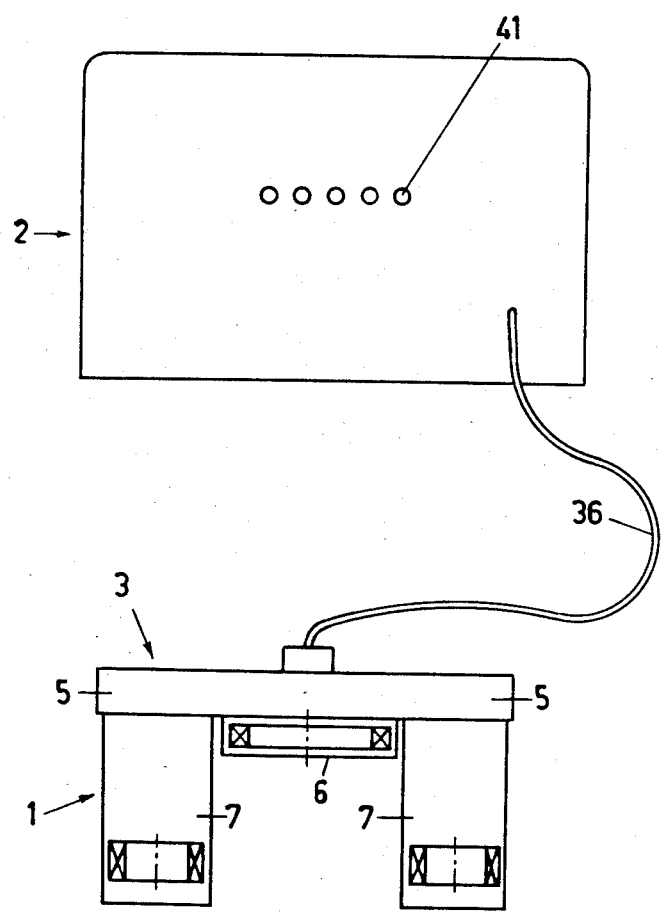
FIG. 3 is a side view of the equipment part of which is shown in FIGS. 1 and 2.
Figure 4:
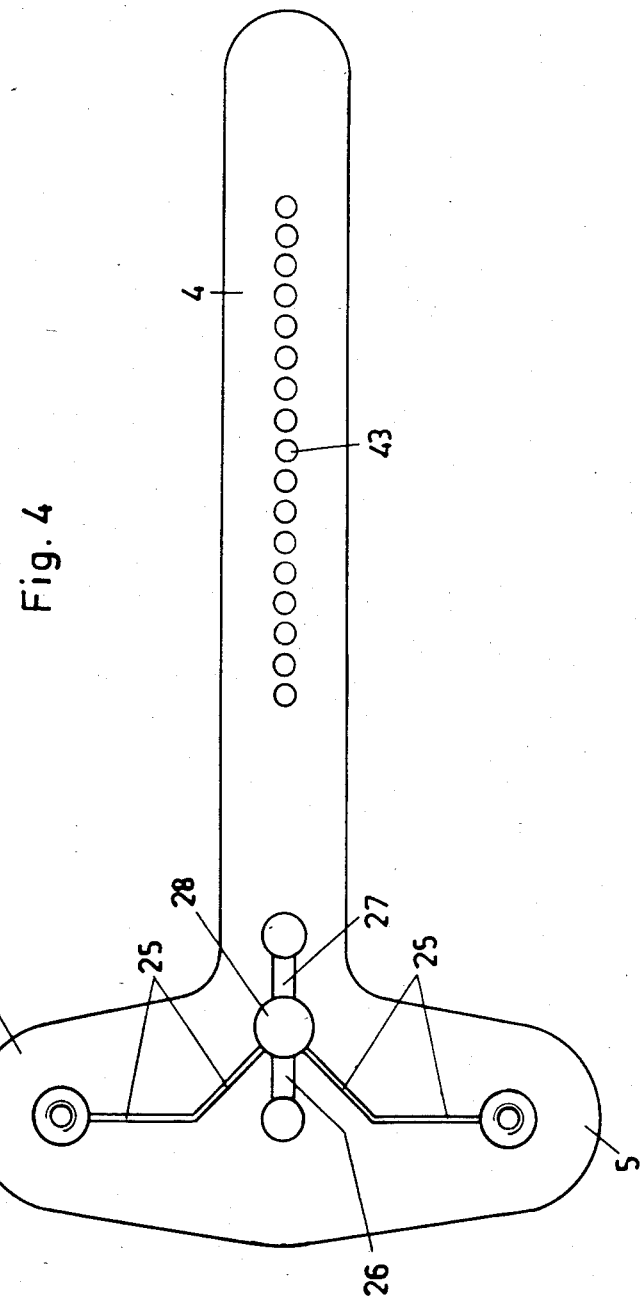
FIG. 4 is a bottom view of part of the equipment as shown in FIGS. 1–3.
Figure 5:
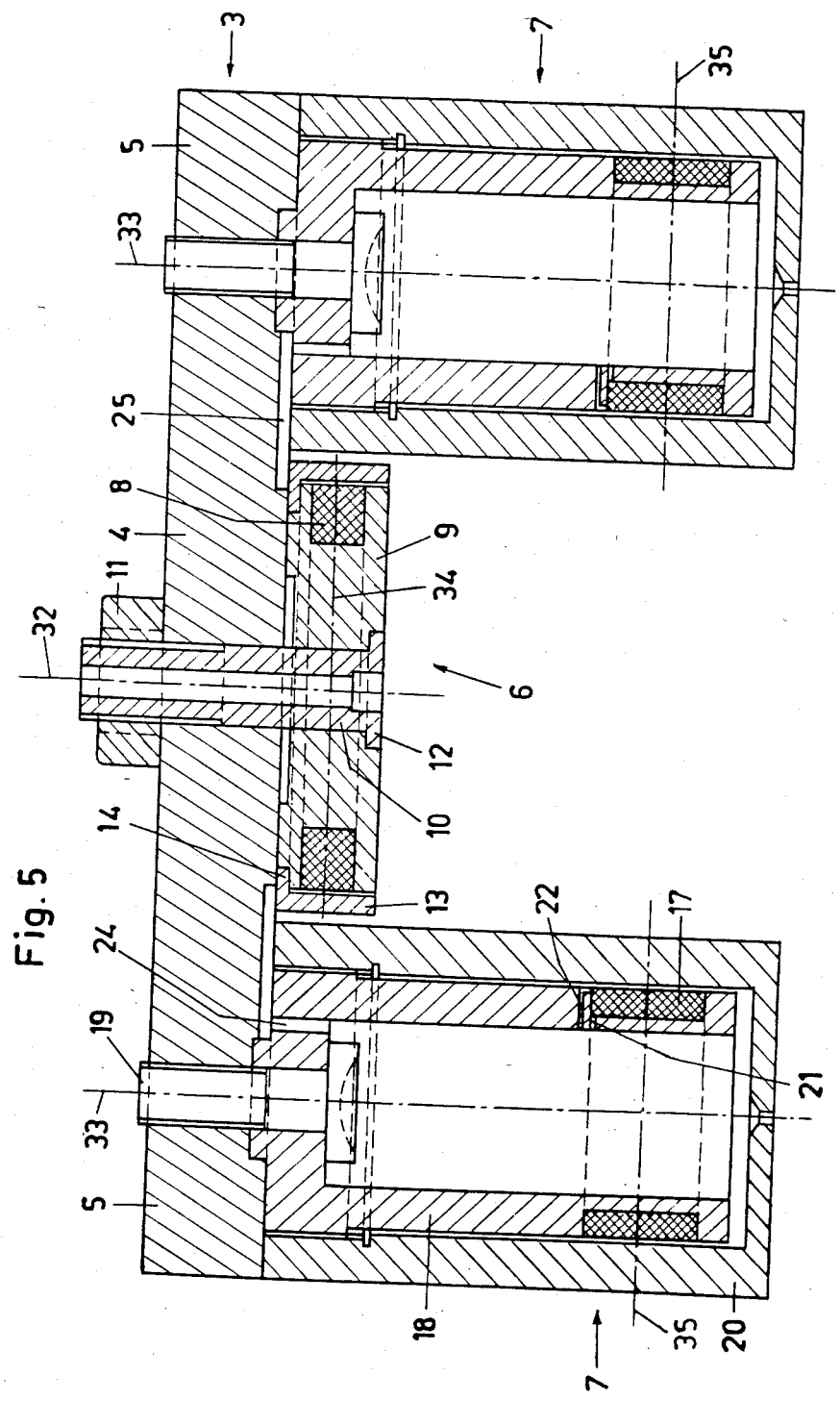
FIG. 5 is a section view on a larger scale, along line V—V in FIG. 1.
Figure 6:
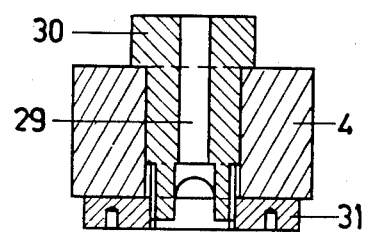
FIG. 6 is a section view on the same scale as FIG. 5, along line VI—VI in FIG. 1.
Figure 7:
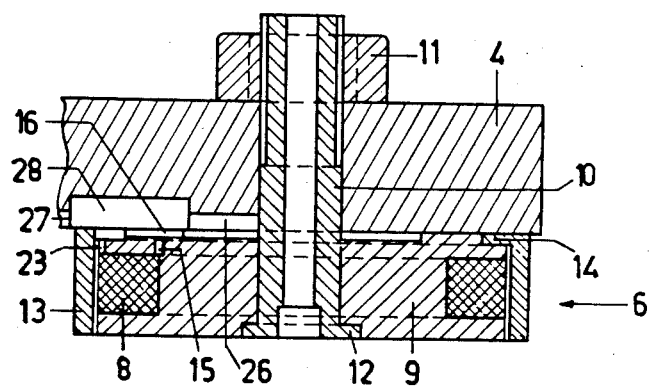
FIG. 7 is a section view on the same scale as FIGS. 5 and 6, along line VII—VII in FIG. 1.

The equipment as shown in the figures is intended for localizing with high accuracy the end of a pin fitted in a bone surrounded by muscle tissue, to make it possible to perform cuts in the muscle tissue and to drill in said bone a cross-wise channel accurately along the axis of the cross-wise channel provided in said pin end for the fitting thereafter of the distal cross-pin.

Fitting of the pin in the bone and arranging the near cross-pin are performed before using the equipment according to the invention, in the way as described in U.S. Pat. No. 4,281,649.

The equipment as shown in the figures is comprised of an electromagnetic sight 1 and an electronic device 2.

The electromagnetic sight comprises a support of plastic material 3 in T shape, comprised of an arm 4 and two legs 5.

Against the lower side of support 3 are mounted three coils: a first self-induction coil 6, which is a radiating coil, and two second self-induction coils 7, which are receiving coils.

The radiating coil 6 is comprised of a winding 8 supported by a core 9 of plastic material secured to the lower surface of arm 4 between the legs 5, by means of a screw bolt-forming tube 10 and a plastic material nut 11. The tube 10 is of a non magnetic metal with high electric conductivity, e.g. of aluminum.

The rim 12 of tube 10 is received into a recess provided in the lower surface of core 9, and the nut 11 bears on the upper side of arm 4.

A plastic-material cap 13 is captured with the rim 14 thereof between the core 9 and the lower surface of arm 4. Said cap 13 covers said winding 8.

A hole 15, a passageway 23 and a groove 16 are provided in a rim of core 9 to let wires (not shown) leading to winding 8, pass through.

The groove is extended in the rim 14 of cap 13.

Each of said receiving coils 7 is comprised of a winding 17 supported by a plastic-material core 18 secured to the lower surface of a leg 5 by means of a plastic-material screw bolt 19 which is screwed in the leg.

A plastic-material cap 20 covers said core 18, on which the cap is screwed, as well as said winding 17.

In the core 18 are provided holes 21, 22, and 24 to let wires (not shown) leading to winding 17, pass through.

The wires (not shown) leading to windings 8 and 17 are guided from said holes 24 and groove 16, through grooves 25, 26, and 27, and a recess 28 towards the inlet to a channel 29 provided in a guide part 30 of plastic material. Said part 30 is mounted in the arm 4, it passes therethrough, and it is retained into said arm by a plate 31 screwed on the end thereof.

The axis 32 of the radiating coil 6 and the axes 33 of the receiving coils 7 lie in one and the same plane.

The symmetry planes 35 of the receiving coils 7 at right angle to the axes 33 thereof coincide with one another and differ from the symmetry plane 34 of the radiating coil 6 at right angle to the axis 32 thereof.

The spacing between the planes 35 on the one hand, and the plane 34 on the other hand depends on the kind of bone to be treated by the equipment and is generally in the range from 1 to 10 cm, and preferably in the range from 6 to 7 cm.

The height of winding 8, that is the dimension thereof along the direction of axis 32, is about 1 cm. The height of windings 17, that is the dimension thereof along the direction of axes 33, depends on the kind of bone to be treated by the equipment and is generally in the range from 2 to 3 cm.

It is essentially due to the relative arrangement of the coils that a large enough phase-shift is caused between the e.m.f. generated in the receiving coils 7 under the action of the electromagnetic field generated by the radiating coil 6 supplied with A.C., when a metal pin lies assymetrically between said coils 7.

Figure 8:
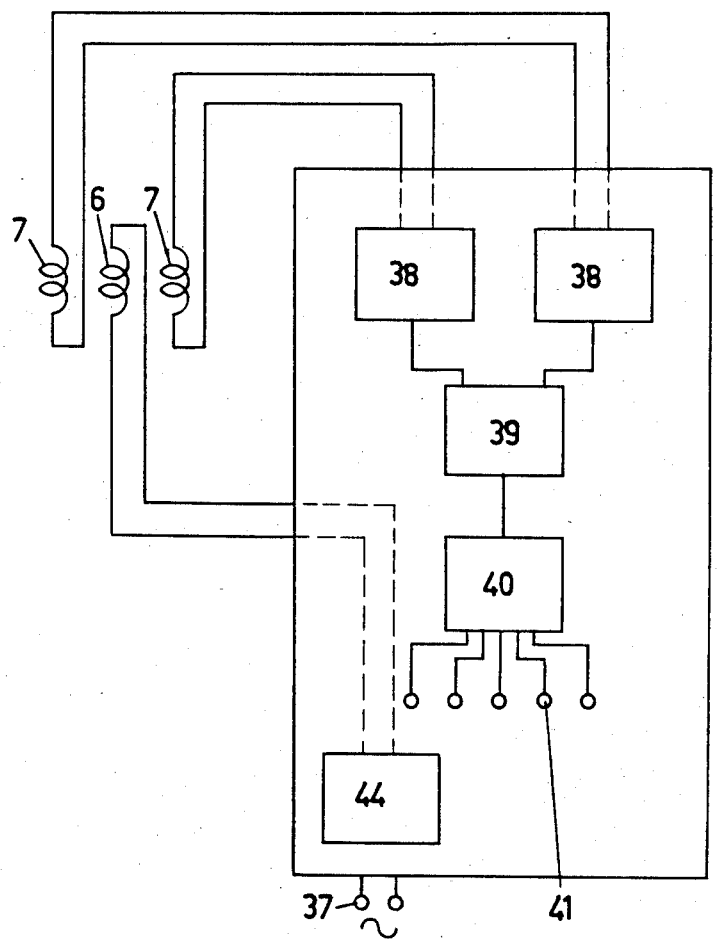
FIG. 8 is a block diagram of the electric part of the equipment as shown in FIGS. 1–7.

The cables 36 comprising the wires leading to windings 8 and 17, connect the electromagnetic sight 1 to the electronic device 2 as shown in the block diagram in FIG. 8.

Said device is supplied from the network 37. Said device comprises an oscillator 44 which couples A.C. to said radiating coil 6. Said radiating coil receives a current with a frequency about 30 kHz. The electromagnetic field being generated induces e.m.f.'s in the receiving coils 7. Said e.m.f.'s are accurately phased when no metal lies between the coils 7, or when between said latter coils lies a metal part which is located perfectly symmetrically relative to said coils.

The electronic device comprises means 38 for amplifying those signals which are generated in the receiving coils 7, means 39 for measuring the phase-shift angle between said amplified signals, and a means 40 for comparing said phase-shift angle relative to two positive thresholds and two negative thresholds. Said comparing means controls in turn five LED's 41, the center one of which is green; on either side thereof lies an orange LED, and at both ends are arranged red LED's. When the measured phase-shift angle is smaller than the thresholds, the center green LED lights up. When the phase-shift angle rises above minimum absolute value positive or negative threshold, the left-hand or right-hand orange LED lights up depending on whether it is the positive threshold or the negative threshold. When the phase-shift angle is larger than the maximum absolute value positive or negative threshold, the left-hand or right-hand red LED lights up, depending on whether it is the positive threshold or the negative threshold.

The symmetry plane 42 of arm 4, enclosing the axis 32 of the radiating coil 6 and at right angle to the plane of the receiving coil axes 33, also encloses the axes of holes 43 which lie in parallel relationship with said axes 32 and 33. Said holes 43 lie at constant intervals.

Said holes 43 correspond to various pins which may be introduced into a bone during an operation. The spacing between the two channels provided in a pin for the fitting of the near and distal cross-pins corresponds to the spacing between the axis of tube 10 and the axis of one of the holes 43.

During an operation, the electromagnetic sight 1 is located stradling the limb to be operated on, in such a way that the sleeve of the template integral with the pin fitted into the broken bone, lies inside a hole 43. The axis of said hole then coincides with the axis of the channel provided in the pin for the near cross-pin, and the receiving coils 7 lie on either side of the limb. The electromagnetic sight 1 may be arranged in such a way due to the free spacing between said receiving coils 7 being large enough to obtain the space required for the limb to be operated on, and said spacing lies for example in the range of 9 to 13 cm.

The surgeon knows which is the hole to be used; it is that hole 43 the axis of which is spaced from the axis of tube 10 with a distance which is accurately equal to the spacing between those two channels which are provided in the pin being used, for the near and distal crosspins. Besides each hole is marked on arm 4, the number or length of the corresponding pin. The surgeon consequently knows which is the hole to be used during the operation being performed, with a particular pin.

The channel in tube 10 may then be accurately located in the extension of the channel provided in the pin for the distal cross-pin.

The tube 10 may guide the drill for drilling accurately the bone at the channel level and for suitably fitting the distal cross-pin. However, it is then required tnat the symmetry plane 42 of arm 4 encloses the pin axis, or in other words that the pin lies midway between the receiving coils 7.

Now there results from the above that when the pin, a metal part, lies accurately midway between the receiving coils 7, the green LED lights up. The axis of the tube 10 then pin-points the distal hole in the pin. A slight discrepancy either way is signaled by the lighting-up of an orange LED. An orange LED lights up for example, when the spacing between the pin and the center line between the receiving coils 7 lies in the range from 0.6 to 0.7 mm. A larger spacing is signaled by the lighting-up of a red LED.

The equipment according to the invention thus allows an accurate localizing of the pin distal channel during the drilling of the bone for the distal cross-pin, and during the fitting of this latter one.

It must be understood that the equipment and more particularly the electronic device may be provided with conventional adjusting means.

It must also be understood that the invention is in no way limited to the described embodiment and that many changes may be brought therein, notably as regards the shape, the number, the arrangement and the composition of the elements used for the embodying thereof, without departing from the scope of this patent application.

I claim:

1. An apparatus for determining the position of a metal body in a medium with low electric conductivity comprising:
   a support means,
   a radiating self-induction coil mounted on said support means,
   an A.C. current source,
   a connecting means connecting the A.C. current source to the radiating self-induction coil, the radiation coil thus generating a radiation,
   two receiving self-induction coils mounted on the support, the radiation of the radiation coil generating signals in the receiving coils, the radiation coil and the two receiving coils having parallel axes, the receiving coils being arranged symmetrically relative to the radiating coil, the radiating coil and the receiving coils having symmetry planes at right angle to said axes, said symmetry planes of the receiving coils coinciding with one another and differing from said symmetry plane of the radiating coil to create an enclosure adapted to receive at least a portion of said medium which contains said metal body and in a space between the receiving coils and facing the radiating coil being free, and
   signaling means, the receiving coils being connected to the signaling means and controling said means according to a phase-shift of the signals generated in the receiving coils by the radiation from the radiating coil.

2. The apparatus of claim 1 in which the A.C. source comprises an oscillator.

3. The apparatus of claim 2 in which the oscillator has a frequency in the range of 30 kHz.

4. The apparatus of claim 1, in which the spacing between the coinciding symmetry planes of the receiving coils and the symmetry plane of the radiating coil lies in the range from 1 to 10 cm.

5. The apparatus of claim 4, in which said spacing is in the range of 6 to 7 cm.

6. The apparatus of claim 4, in which the axial height of the radiating coil is about 1 cm.

7. The apparatus of claim 4, in which the axial height of the receiving coils is in the range of 2 to 3 cm.

8. The apparatus of claim 1, in which there is a free space between the receiving coils in the range of about 9 to 13 cm.

9. The equipment of claim 1, in which said support means comprises an arm, said arm having a symmetry plane, the symmetry plane of said arm enclosing the axis of the radiating coil and lying at right angle to a plane comprising the axis of the radiating coil and the axes of the two receiving coils, the radiating coil and the arm having a channel co-axial with the radiating coil, the arm being provided with a series of holes, said holes having axes lying in the symmetry plane of the arm and being in parallel relationship with the axes of the radiating coil and of the receiving coils, the A.C. source and the signaling means being part of an electronic device, and the radiating coil and the receiving coils being connected by cables to the electronic device.

10. The apparatus of claim 9, in which the axes of the holes are at constant intervals.

11. The apparatus of claim 9, in which the channel comprises a tube.

12. The apparatus of claim 11, in which the tube is of a non-magnetic metal with high electric conductivity.

13. The apparatus of claim 1, in which said signaling means comprises visual indicators arranged in line, said visual indicators comprising a central visual indicator showing a minimum phase shift.

14. The apparatus of claim 13, in which some of these visual indicators are varied in color depending on the spacing thereof from the central indicator.

* * * * *